United States Patent
Di Maio, Jr. et al.

[11] Patent Number: 5,824,095
[45] Date of Patent: Oct. 20, 1998

[54] ANATOMICALLY NEUTRAL JOINT

[75] Inventors: William G. Di Maio, Jr., Boothwyn; Michele Staud Marcolongo, Lansdowne, both of Pa.; Arnold-Peter C. Weiss, Barrington, R.I.

[73] Assignees: E. I. du Pont de Nemours and Company, Wilmington, Del.; De Puy DuPont Orthopedics, Warsaw, Ind.

[21] Appl. No.: 842,166

[22] Filed: Apr. 23, 1997

Related U.S. Application Data

[60] Provisional application No. 60/017,477 Apr. 26, 1996.
[51] Int. Cl.⁶ ....................................................... A61F 2/42
[52] U.S. Cl. ............................................. 623/18; 623/18
[58] Field of Search ........................................ 623/18, 21

[56] References Cited

U.S. PATENT DOCUMENTS

| | | | |
|---|---|---|---|
| 3,462,765 | 8/1969 | Swanson | 3/1 |
| 3,593,342 | 7/1971 | Niebauer et al. | 3/1 |
| 3,681,786 | 8/1972 | Lynch | 3/1 |
| 4,246,662 | 1/1981 | Pastrick | 3/1.91 |
| 4,367,562 | 1/1983 | Gauthier | 3/1.91 |
| 4,871,367 | 10/1989 | Christensen et al. | 623/21 |

FOREIGN PATENT DOCUMENTS

| | | | |
|---|---|---|---|
| 0 042 808 | 12/1981 | European Pat. Off. | A61F 1/03 |
| 2026653 | 1/1995 | Russian Federation | A61F 2/42 |
| 1 320 956 | 6/1973 | United Kingdom | A61F 1/00 |
| WO 95/17861 | 7/1995 | WIPO | A61F 2/42 |

*Primary Examiner*—Randy C. Shay

[57] ABSTRACT

A joint prosthesis is disclosed with stems affixed to the flexing main body at a natural, angle; with positive flexion and extension stops; and with stress-relieving radii at intersections between the stems and the main body.

15 Claims, 2 Drawing Sheets

ANATOMICALLY NEUTRAL JOINT

BACKGROUND OF THE INVENTION

This application claims the benefit of U.S. Provisional application Ser. No. 60/017,477, filed Apr. 26, 1996.

FIELD OF THE INVENTION

This invention relates to surgically implantable prosthetic finger joints and a design for such joints which permits a wider range of use and provides a more natural appearance. The joints of this invention exhibit an anatomically neutral resting position and are fitted with anatomically correct flexion limits.

DESCRIPTION OF THE PRIOR ART

U.S. Pat. No. 4,871,367, issued Oct. 3, 1989 on the application of Christensen et al., discloses a prosthetic knuckle implant wherein the implant stems are in a straight line and the flexion limits are incomplete.

U.S. Pat. No. 3,462,765, issued Aug. 26, 1969 on the application of Swanson discloses a straight rubber joint prosthesis for implantation into hands.

U.S. Pat. No. 3,993,342, issued Jul. 20, 1971 on the application of Niebauer et al, discloses a straight flexible plastic joint prosthesis having a narrowed body to facilitate flexibility and movement of the joint.

Russian Patent No. RU 2,026,653, published Jan. 20, 1995, discloses a prosthetic knuckle joint in which the stems of the joint are at an angle with one another.

SUMMARY OF THE INVENTION

A surgically implantable, anatomically neutral, joint, comprising a one-piece main body of flexible, elastomeric, material including first and second spaced-apart end sections with first and second outer faces and a thinner web section extending between and joining said end sections for flexing movement about a particular flexing axis through the web section section, whereby the first and second outer faces are diverging toward the top of the main body and the main body functions as a hinge with said end sections and said web section together defining a v-shaped groove across the top of the main body, having first and second v-shaped groove sides converging toward each other, and extending into the main body; and a key-hole shaped groove across the bottom of the main body, having a key-hole hole segment of circular cross-section through the main body defining the bottom of the web section, and first and second key-hole side segments converging toward each other, extending into the main body, and opening into said key-hole hole segment between said end sections; and first and second stems of flexible, elastomeric, material connected to and extending out from and perpendicular with the first and second end sections of said main body in directions normal to said flexing axis and away from one another, said first and second stems being implantable within cooperating intramedullary canals of adjacent bones, defining said joint.

DETAILED DESCRIPTION

In the art of surgically implantable prostheses, there is a continual search for devices which provide more natural appearance and more convenient, efficient, and long-lasting use.

The prosthetic joint of this invention permits a natural appearance by its anatomically neutral design. By "anatomically neutral" is meant that the joint is made such that a hand or finger utilizing the joint is in a normal, slightly flexed, attitude at rest. For example, the proximal phalanx relative to the metacarpal is 20 to 30 degrees in flexion. Anatomic neutrality is important not only for the sake of appearance but, also, because it provides significant functional benefit. The usual, straight-through, prosthetic knuckle device with the stems set at 180 degrees, requires that the phalangeal stem portion of the joint must be rotated nearly 30 degrees in flexion and maintained in that position by constant use of muscle force just to achieve a natural appearance. The present device achieves a natural appearance with muscles relaxed. In addition, the present device permits full flexion using considerably reduced energy because the present device is at rest within, and near the middle of, the desired range of motion rather than at the extreme, near full extension.

The device of this invention finds utility joining metacarpal and proximal phalanx bones as a prosthetic metacarpal phalangeal joint and, also, joining proximal phalanx and middle phalanx bones as a prosthetic proximal interphalangeal joint.

Figure 1:
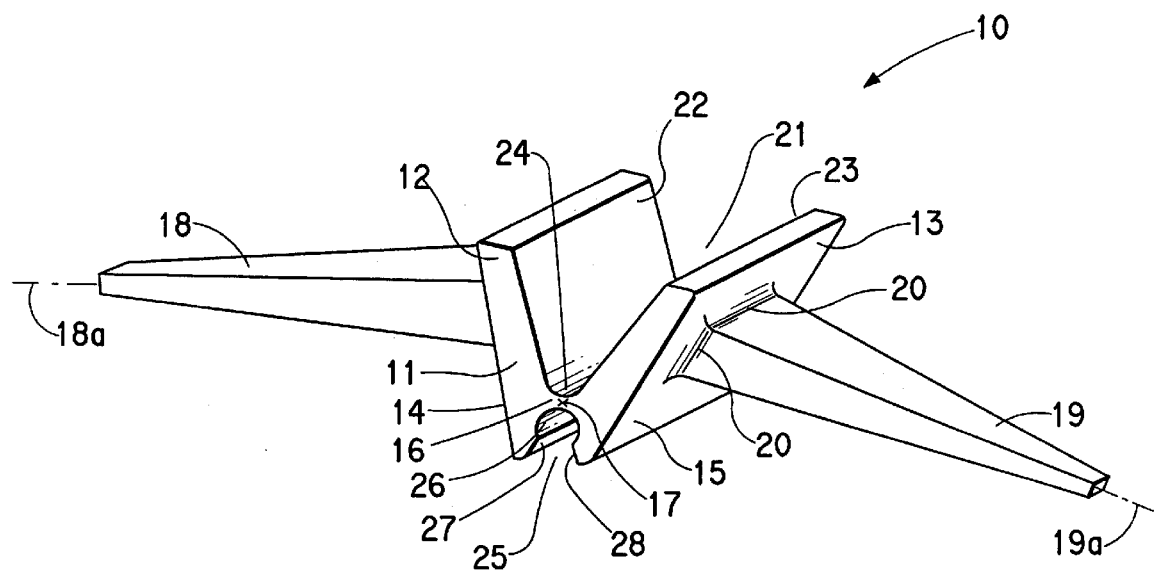
FIG. 1 is a perspective view of the joint of this invention.

Referring now to FIG. 1, surgically implantable finger joint 10 of this invention comprises a one-piece main body 11 with spaced-apart end sections 12 and 13—each having outer faces 14 and 15, respectively. Main body 11 has a thin web section 16 between end sections 12 and 13. It is web section 16 which provides for flexing or hinge movement of the joint and which includes flexing axis 17 extending through web section 16.

Stems 18 and 19 are connected to end sections 12 and 13, respectively, and are adapted for implantation within cooperating intramedullary canals in adjacent bones. Stems 18 and 19 have longitudinal axes 18a and 19a, respectively, and those axes are perpendicular with outer faces 14 and 15, respectively. Stems 18 and 19 can have round, square, or other cross-sectional shape and are generally sized to be small at the outer end and larger closer to the end sections.

The inventors herein have discovered that breakage of the stems from the main body, which has in the past been a considerable problem, can be greatly mitigated or eliminated by providing radii of at least 0.07 centimeter at the intersections 20 of the stems with the outer faces. It has been determined that sharp corners at intersections 20 greatly increases the likelihood of rupture and tear propagation between the stem and the main body and that a radius of 0.07 to 0.13 centimeter dramatically relieves stresses in the material at those points and, thereby, reduces the likelihood of failure. A radius of about 0.075 centimeter is preferred.

In order to maintain a natural angle for the finger joint, main body 11 is constructed to have outer faces 14 and 15 diverging upward toward the top of the main body at an angle of 20 to 40, preferably about 30, degrees. Having such an angle, at rest, permits a user to both, flex and extend the knuckle using muscle forces. Starting from a knuckle position which is straightened at 180 degrees, it is desirable that 5 to 40, preferably 10 to 20, degrees of further extension should be possible; and, with that in mind, v-shaped groove 21 across the top of main body 11 is made having v-shaped groove sides 22 and 23 converging toward each other into main body 11 at an angle of 25 to 80, preferably 45, degrees. As the knuckle is extended, groove sides 22 and 23 are moved closer together and the extension limit is reached when the groove sides meet. In the neutral or resting position of the knuckle, groove sides 22 and 23 can join at the end of the groove in a radius 24 which is 0.07 to 0.23, preferably 0.17, centimeter.

Again, starting from a knuckle position which is straightened at 180 degrees, it is desirable that 85 to 95, preferably 90, degrees of flexion should be possible. Key-hole shaped groove 25 across the bottom of main body 11 is made having a key-hole hole segment 26 of circular cross-section through main body 11. Hole segment 26 defines the bottom, and radius 24 of v-shaped groove 21 defines the top of web section 16. Key-hole side segments 27 and 28 converge toward hole segment 26 at an angle of 50 to 85, preferably 60, degrees. As the knuckle is flexed, side segments 27 and 28 are moved closer together and the flexion limit is reached when the side segments come together.

The key-hole construction is used for flexion due to the desire for a clear limit to flexion extreme. Key-hole hole segment 26 permits compression of web section 16 without interference by material at the bottom of the key-hole shaped groove and contact of side segments 27 and 28 provides a sure limit to the range of movement. V-shaped groove 21 can, also, be constructed to include a key-hole hole segment. However, because the primary function for implanted finger joints is to restore grasping, flexion is more important than extension and there is less need for a sure limit to the range of movement for extension of the knuckle. The key-hole construction is, therefore, not so important for v-shaped groove 21.

The nature of the material used in construction of main body 11 and the thickness of web section 16 can be used to control flexing stiffness of the joint. Suitable elastomeric materials are resilient, biocompatible and resistant to tearing. Such elastomeric materials may include silicone rubber, polyurethane rubber, polyurethane urea rubber, rubber reinforced polypropylene, polycarbonate based polyurethane, and the like. One characteristic by which an elastomer can be evaluated is called Durometer hardness. Durometer hardness is defined by ASTM test number D-2240. In general, the hardness of an elastomer is reported as a number and a Shore designation. The number is on a scale of 10 to 100, the higher the number the harder the elastomer. The Shore designation determines the hardness test method and equipment, and is designated by letters A through D. Generally, as the Shore A hardness of a material increases, the modulus of elasticity for that material also increases—leading to a stiffer joint.

Moreover, the joint can be made from more than one material or it can be made from a single material treated to exhibit different characteristics in different sections. As an example, a joint can be made using rubber reinforced polypropylene with a Durometer hardness of 64 Shore A for web section 16, which serves as a flexing hinge, and a Durometer hardness of 87 Shore A for the remainder of the joint. The joint of this invention is preferably made from elastomers having a hardness of 45 to 100.

In joints having material of different characteristics in different sections, the hinge or web section should have a Durometer hardness of about 45 to 80 Shore A and the stem sections should have a Durometer hardness higher than that for the web section and within the range of 75 to 100 Shore A.

EXAMPLE 1

This example describes flexural fatigue test results for a finger joint prosthesis of the current invention and for two commercially available finger joint prostheses. The implants of the current invention displayed a higher resistance to tear formation during flexural fatigue testing than prior art implants.

Metacarpophalangeal joint prostheses of the current invention (size 40) were prepared from a silicone rubber having a Durometer hardness of 55 Shore A by injection molding according to the general design shown in FIG. 1, except that the corners of the end sections 12 and 13 were rounded. The outer faces 14 and 15 diverged upward toward the top of the main body at an angle of 30 degrees with the inner groove sides 22 and 23 joining at the end of groove 21 in a radius 24 of 0.066 in (0.168 cm). The intersection 20 of the stems with the outer faces had a radius of 0.040 in (0.102 cm). The key-hole shaped groove 25 across the bottom of the main body included first and second key-hole side segments 27 and 28 converging at an angle of 75 degrees and a key-hole hole segment 26 having a radius of 0.050 in (0.127 cm). The thickness of the web section 16 was 0.090 in (0.229 cm). Four implants of the current invention were gas plasma sterilized (4 hr cycle) prior to testing and two unsterilized joints were also tested.

Figure 2A:
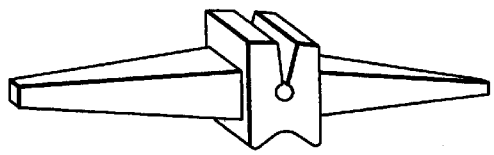
FIG. 2A and FIG. 2B are perspective views of prior art joint prostheses.
Figure 2B:
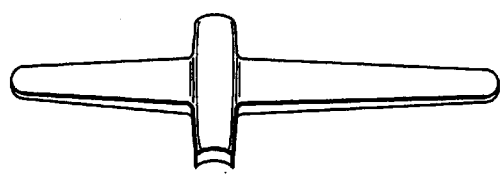

Commercially available sterilized metacarpophalangeal joint prostheses were tested for comparison with the implants of the current invention. Three size 40 AVANTA MCP joints (commercially offered by Avanta, San Diego, Calif.) having a design described in U.S. Pat. No. 4,871,367 with a keyhole-shaped groove on the top and a V-shaped groove on the bottom, as shown in FIG. 2A, and five size 6 Swanson MCP joints (commercially offered by Wright Medical, Arlington, Tenn.) having a design described in U.S. Pat. No. 3,462,765 and shown in FIG. 2B were used. The implants were all of equivalent size. A flexural fatigue machine was set to cycle the implants through a total 90 degree rotation ranging from 5 degrees of extension to 85 degrees of flexion. The angles of extension and flexion are measured relative to the finger being in a straightened state where the axes of the two stems are at an angle of 180 degrees. The collets which supported the stem region of the implants during testing were machined to the profile of the stem so that there would be adequate support of the stem (representing bone support in vivo) while allowing the stem to piston in an unconstrained fashion (again, as seen in vivo). The implants were immersed in a 37 degrees C. recirculating saline bath buffered to a pH of 7.4 to simulate the environment in the body, and cycled at 3 Hz for a total of ten million cycles. After approximately every half million cycles, the implants were removed from the test machine, dried, and visually inspected under a light microscope at 40×. Both the palmar and dorsal sides of the hinge were examined for signs of damage.

The implants of the current invention survived the ten million cycles of fatigue with negligible damage. No visible damage was observed on three of the four sterilized implants. One implant showed the initiation of a small tear (0.025 mm wide and 1.6 mm in length) on the palmar surface of the hinge after 2.5 million cycles. The tear after ten million cycles measured 0.05 mm in width and 3 mm in length. Of the unsterilized implants, one implant had no visible damage while the other had a slight tear on the palmar surface of the hinge, first observed at 4.1 million cycles and progressing slightly over the duration of the fatigue cycling to a final width of 0.037 mm and 3 mm in length. No other anomalies were observed on the implants.

The three AVANTA MCP implants showed some minimal damage during testing, with all implants displaying a similar damage mode over time. Small voids were observed spaced along the entire length of the palmar surface of the hinge after 2.4 million cycles, the voids ranging from 0.125 to 0.200 mm in width and 0.125 to 1 mm in length. Over time, these voids coalesced to form a closely associated series of voids, resulting in a small tear spanning the entire width of the palmar surface of the hinge after ten million cycles. The failure sites are similar to those reported in clinical failures of AVANTA MCP implants.

The Swanson MCP implants also showed some damage during testing, with each of the five implants displaying the same damage mode over time. Tears formed in the proximal stem/hinge interface on the palmar surface, with the tears first observed after two million cycles and progressing through ten million cycles. After two million cycles, the tears measured 1.24–3.75 mm in length and progressed to a crack opening more and penetrating into the depth of the part to a greater degree after ten million cycles. This mode of damage is consistent with failure sites reported clinically for the Swanson MCP implants.

EXAMPLE 2

A finite element analysis was performed on an anatomically neutral metacarpophalangeal joint of the current invention and compared to the AVANTA MCP joint described in Example 1 using the advanced nonlinear ABAQUS finite element code. In this example, the joint of the current invention was identical to that described in Example 1 except that the stem profiles were rounded and the angle at which segments 27 and 28 converged was 60 degrees.

Figure 3:
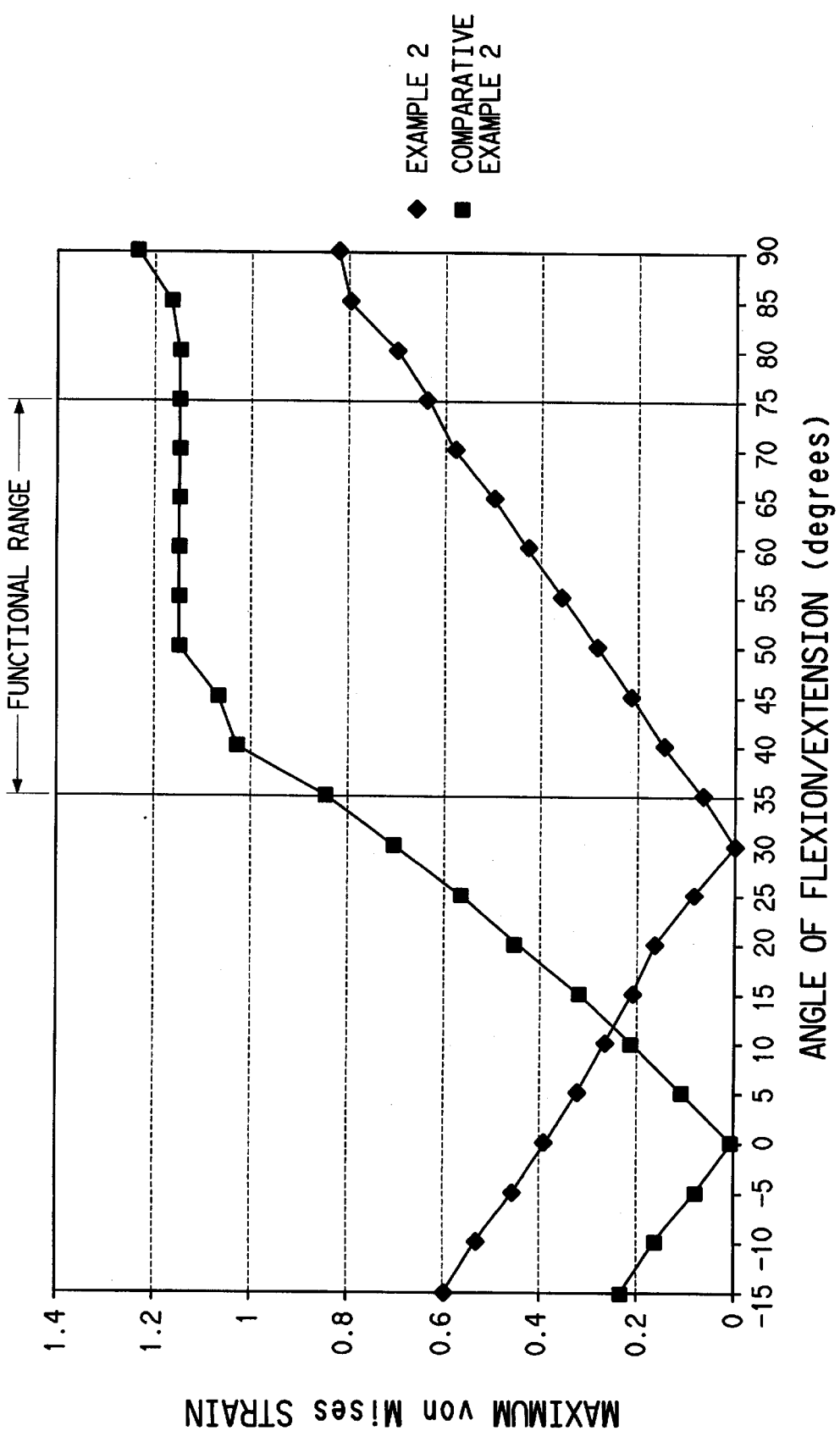
FIG. 3 is a plot comparing the maximum von Mises strain versus angle of flexion/extension of the joint of this invention to that of a prior art joint.

The results of the finite element analysis are shown in FIG. 3 which is a plot of the maximum von Mises strain versus the angle of flexion/extension for each design. In this example, an angle of zero degrees corresponds to the finger being in a straightened state where the axes of the two stems are at an angle of 180 degrees. Negative angles are angles of extension and positive angles are angles of flexion. The angles which range from 35–75 degrees represent the functional range of motion for a patient performing daily activities and are the regions in which most movement is performed. In the functional range, it is clear that the metacarpophalangeal joint of the current invention has significantly lower strain than the AVANTA MCP joint. This indicates that the AVANTA MCP joint is strained much more through the functional range of motion, thus stressing the material to a greater degree, potentially resulting in a reduced fatigue life of the implant.

The superior results obtained for the metacarpophalangeal implant of the current invention shown in FIG. 3 is believed to result from the synergistic combination of two factors: the 30 degree bend and the keyhole geometry in the palmar hinge region in the metacarpophalangeal joint of the current invention versus the straight geometry and V-shaped groove in the palmar hinge of the AVANTA MCP joint.

What is claimed is:

1. A surgically implantable, anatomically neutral, joint, comprising:
   (a) a one-piece main body of flexible, elastomeric, material including first and second spaced-apart end sections with first and second outer faces and a thinner web section extending between and joining said end sections for flexing movement about a particular flexing axis through the web section, whereby the first and second outer faces are at an angle from 20 to 40 degrees from each other, and are diverging toward the top of the main body, the main body functions as a hinge with said end sections and said web section together defining
      (i) a v-shaped groove across the top of the main body, having first and second v-shaped groove sides converging into the main body; and
      (ii) a key-hole shaped groove across the bottom of the main body, having a key-hole hole segment of circular cross-section through the main body defining the bottom of the web section, and first and second key-hole side segments converging into the main body, and opening into said key-hole hole segment between said end sections; and
   (b) first and second stems of flexible, elastomeric, material connected to and extending out from and perpendicular with the first and second end sections of said main body in directions normal to said flexing axis, the intersections of said first and second stems with said first and second outer faces having radii of at least 0.07 centimeter and said first and second stems being implantable within cooperating intramedullary canals of adjacent bones, defining said joint.

2. The joint of claim 1 wherein the first and second v-shaped groove sides converge at an angle of from 25 to 80 degrees toward each other.

3. The joint of claim 2 wherein the first and second v-shaped groove sides end by joining in a radius of from 0.07 to 0.23 centimeter.

4. The joint of claim 1 wherein the first and second key-hole side segments converge at an angle of from 50 to 85 degrees toward each other.

5. The joint of claim 1 wherein the radii at the intersections of the first and second stems with the first and second outer faces are from 0.07 to 0.13 centimeter.

6. The joint of claim 1 wherein the flexible material exhibits a Durometer hardness of 45 to 100 Shore A.

7. The joint of claim 1 wherein the flexible material of the web section between the end sections exhibits a Durometer hardness of 45 to 80 Shore A, and the flexible material of the remainder of the joint exhibits a Durometer hardness higher than that for the web section and within the range of 75 to 100 Shore A.

8. The joint of claim 1 wherein the flexible, elastomeric, material is selected from the group consisting of silicone rubber, polyurethane rubber, polyurethane urea rubber, rubber reinforced polypropylene and polycarbonate based polyurethane.

9. A surgically implantable, anatomically neutral, joint, comprising:
   (a) a one-piece main body of flexible, elastomeric, material including first and second spaced-apart end sections with first and second outer faces and a thinner web section exhibiting a Durometer hardness of 45 to 80 Shore A and extending between and joining said end sections for flexing movement about a particular flexing axis through the web section, whereby the first and second outer faces are at an angle from 20 to 40 degrees from each other, and are diverging toward the top of the main body, the main body functions as a hinge with said end sections and said web section together defining
      (i) a v-shaped groove across the top of the main body, having first and second v-shaped groove sides converging into the main body; and
      (ii) a key-hole shaped groove across the bottom of the main body, having a key-hole hole segment of circular cross-section through the main body defining the bottom of the web section, and first and second key-hole side segments converging into the main body, and opening into said key-hole hole segment between said end sections; and (b) first and second stems of flexible, elastomeric, material exhibiting a Durometer hardness higher than that for the web section and within the range of 75 to 100 Shore A and connected to and extending out from and perpendicular with the first and second end sections of said main body in directions normal to said flexing axis, said first and second stems being implantable within cooperating intramedullary canals of adjacent bones, defining said joint.

10. The joint of claim 9 wherein the first and second v-shaped groove sides converge at an angle of from 25 to 80 degrees toward each other.

11. The joint of claim 10 wherein the first and second v-shaped groove sides end by joining in a radius of from 0.07 to 0.23 centimeter.

12. The joint of claim 11 wherein the first and second key-hole side segments converge at an angle of from 50 to 85 degrees toward each other.

13. The joint of claim 9 wherein the intersections of said first and second stems with said first and second outer faces have radii from 0.07 to 0.13 centimeter.

14. The joint of claim 9 wherein the flexible, elastomeric, material is selected from the group consisting of silicone rubber, polyurethane rubber, polyurethane urea rubber, rubber reinforced polypropylene and polycarbonate based polyurethane.

15. A surgically implantable, anatomically neutral, joint, comprising:

(a) a one-piece main body of flexible, elastomeric, material including first and second spaced-apart end sections with first and second outer faces and a thinner web section extending between and joining said end sections for flexing movement about a particular flexing axis through the web section, whereby the first and second outer faces are at an angle from 20 to 40 degrees from each other, and are diverging toward the top of the main body, the main body functions as a hinge with said end sections and said web section together defining (i) a v-shaped groove across the top of the main body, having first and second v-shaped groove sides converging into the main body at an angle of from 25 to 80 degrees toward each other; and (ii) a key-hole shaped groove across the bottom of the main body, having a key-hole hole segment of circular cross-section through the main body defining the bottom of the web section, and first and second key-hole side segments converging into the main body at an angle of from 50 to 85 degrees toward each others and opening into said key-hole hole segment between said end sections; and (b) first and second stems of flexible, elastomeric, material connected to and extending out from and perpendicular with the first and second end sections of said main body in directions normal to said flexing axis, said first and second stems being implantable within cooperating intramedullary canals of adjacent bones, defining said joint.

* * * * *